United States Patent [19]

Hirota et al.

[11] Patent Number: 4,758,376

[45] Date of Patent: Jul. 19, 1988

[54] PHOSPHATE SURFACTANT BASED DETERGENT COMPOSITIONS

[75] Inventors: Hajime Hirota, Megurohon; Hidekazu Ogino, Funabashi; Hideko Ishido, Tokyo; Yutaka Shibata, Yamato; Sahoko Igarashi, Tokyo; Chizuru Fukami, Ichikawa, all of Japan

[73] Assignee: Kao Corporation, Tokyo, Japan

[21] Appl. No.: 931,810

[22] Filed: Nov. 18, 1986

[30] Foreign Application Priority Data

Nov. 28, 1985 [JP] Japan ................... 60-267936
Dec. 2, 1985 [JP] Japan ................... 60-271258
Dec. 12, 1985 [JP] Japan ................... 60-279934
Dec. 12, 1985 [JP] Japan ................... 60-279935

[51] Int. Cl.$^4$ .......... C11D 1/94; C11D 1/32; C11D 1/34; A61K 7/06
[52] U.S. Cl. ............... 252/545; 252/174.16; 252/546; 252/DIG. 5; 252/DIG. 13; 252/DIG. 17; 424/70
[58] Field of Search ........... 252/174.16, 545, 546, 252/DIG. 5, DIG. 13, DIG. 17; 424/70

[56] References Cited

U.S. PATENT DOCUMENTS

| | | | |
|---|---|---|---|
| 3,728,447 | 4/1973 | Osipow et al. | 252/545 |
| 4,132,679 | 1/1979 | Tsutsumi et al. | 252/545 |
| 4,139,485 | 2/1979 | Imokawa et al. | 252/DIG. 13 |
| 4,259,204 | 3/1981 | Homma | 252/174.16 |
| 4,363,755 | 12/1982 | Uchino et al. | 252/174.16 |
| 4,381,259 | 4/1983 | Homma et al. | 252/DIG. 13 |
| 4,438,096 | 3/1984 | Preston | 424/70 |
| 4,479,893 | 10/1984 | Hirota et al. | 252/545 |
| 4,534,964 | 9/1985 | Herstein et al. | 252/545 |

FOREIGN PATENT DOCUMENTS

| | | | |
|---|---|---|---|
| 072093 | 6/1981 | Japan | 252/174.16 |
| 074196 | 4/1984 | Japan | 252/546 |

*Primary Examiner*—Paul Lieberman
*Assistant Examiner*—Linda D. Skaling
*Attorney, Agent, or Firm*—Oblon, Fisher, Spivak, McClelland & Maier

[57] ABSTRACT

The detergent compositions of the present invention comprising a phosphate surfactant and an amidoamine amphoteric surfactant; a hydroxysulfobetaine, aliphatic lactylate, or aliphatic glycolate, have excellent foam characteristics such as foaming property, foaming power, and rapidity of foaming, as well as excellent low-temperature stability, detergency, and mildness to the skin and hair. Therefore, these compositions can be effectively employed for shampoos and cleaning agents for infants which require not only good detergency but also a low incidence of skin irritation.

2 Claims, No Drawings

PHOSPHATE SURFACTANT BASED DETERGENT COMPOSITIONS

BACKGROUND OF THE INVENTION

1. Field of the Invention

The present invention relates to detergent compositions.

2. Description of the Prior Art

Recently, it has been recognized that phosphate surfactants, a kind of anionic surfactant, are very mild surfactants having a low stimulus to the skin. For this reason, they are employed as a component of detergent compositions.

However, such phosphate surfactants have several disadvantages such as deficiency of foaming ability, foaming power, and low-temperature stability, all of which are essential properties required for detergent compositions. Thus, they are not yet deemed satisfactory as surfactants for detergent compositions. Therefore, there has been a demand for improvements in the properties of detergent compositions containing phosphate surfactants while preserving the advantageous characteristics of phosphate.

Alkyl phosphate can generally be obtained as a mixture of monoalkyl phosphate and dialkyl phosphate; thus phosphate surfactants contain dialkyl phosphate having poor water solubility and poor foaming power. Accordingly, when these alkyl phosphates are used as a detergent base for shampoo or skin cleaner, it is necessary to use surfactants in which the monoester content is as much as possible or in which ethylene oxide is added to alkyl groups so as to increase water solubility.

In addition, since there are problems with respect to foaming power and low-temperature stability if such particular alkyl phosphates are singly used as the main components of the detergents, a method in which auxiliaries are further added to detergents has been proposed (Japanese Patent Publication No. 51991/1983, and Japanese Patent Application Laid-Open Nos. 49698/1982, 103598/1983, and 74196/1984).

However, although all of these methods may improve the properties compared with single use of an alkyl phosphate, there still remain problems in that foaming power and low-temperature stability are insufficient as compared with detergents containing other ordinary surfactants as a main agent, and in that the low irritation characteristic specific to alkyl phosphates is lost. Of these methods, a method in which sulfobetaine is used as an auxiliary (Japanese Patent Publication No. 51991/1983) is a relatively excellent method from the veiwpoint of the increase in foaming power and the improvement in low-temperature stability. However, according to this method, propanesultone, which involves some fear of carcinogenesis, must be used to produce the sulfobetaine, so that the method is quite disadvantageous to industrial production of the sulfobetaine.

Further, it should be noted that the phosphate surfactants are likely to give unfavorable feeling to touch to the hair because they produce a calcium salt as they contact with water when they are rinsed, and the salt is adhered to the hair to impair the smoothness of the hair. Thus, the phosphate surfactants are not necessarily satisfactory as surfactant usable for preparing detergent compositions including shampoo compositions.

In order to ameliorate these problems, a method in which a conditioning agent such as an oil is added to a shampoo base has been generally employed. However, this method involved problems in that the addition of the conditioning agent greatly decreases the foaming and cleaning power which are the basic functions of detergents such as shampoo. Their value as commodities is thus remarkably deteriorated.

Therefore, for detergents containing phosphate surfactants, there has been a demand for improvements in their characteristics, particularly, the foam characteristics.

SUMMARY OF THE INVENTION

The present invention made earnest studies in order to solve the above described drawbacks residing in detergent compositions containing phosphate surfactants. As a result, they found that combination use of a particular compounds with a phosphate surfactant not only improves the poor foaming property which is the drawback of such detergent compositions, but also gives good effects of the compositions, such as excellent foaming power and rapidity of foaming. Further, it improves low-temperature stability and a conditioning effect, while causing no change in the detergency and low susceptibility to skin and scalp irritation, which are inherently possessed by the phosphate surfactants. The present invention was accomplished based on the above findings.

Namely, the present invention provides detergent compositions comprising the following components (A) and (B):

(A) one or more phosphate surfactants represented by the following formula (I) or (II):

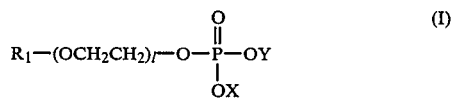

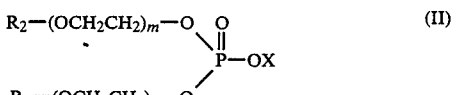

wherein $R_1$, $R_2$, and $R_3$ each independently represent a saturated or unsaturated hydrocarbon group having 8 to 18 carbon atoms; X and Y each independently represent a hydrogen atom, an alkali metal, ammonium, or an alkanol amine having one or more hydroxyalkyl groups having 2 to 3 carbon atoms; and l, m, and n each independently represent an integer of 0 to 10, (B) a compound selected from the group consisting of the following compounds (1) to (3):

(1) an amidoamine amphoteric surfactant represented by the following formula (III) or (IV):

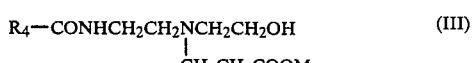

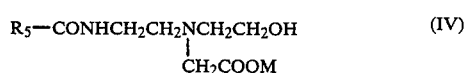

wherein $R_4$ and $R_5$ each independently represent a saturated or unsaturated hydrocarbon group having 7 to 19 carbon atoms; M represents a hydrogen atom, an alkali metal, ammonium, or an alkanol amine having one or more hydroxyalkyl group having 2 to 3 carbon atoms, (2) hydroxysulfobetaine represented by the following formula (V):

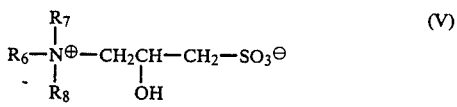

wherein $R_6$ represents a saturated or unsaturated hydrocarbon group having 8 to 18 carbon atoms, and $R_7$ and $R_8$ each independently represent a methyl or ethyl group, and (3) a compound represented by the following formula (VI) and its salt:

wherein RCO represents a linear or branched aliphatic acyl group having 6 to 22 carbon atoms; A represents $CH_3$ or a hydrogen atom, and p represents an integer of 1 to 3.

DETAILED DESCRIPTION OF THE INVENTION AND PREFERRED EMBODIMENTS

As the phosphate surfactant which is the component (A) of the present invention, it is preferable to use a compound having 0 to 3 moles of ethylene oxide added thereto, and more preferably, a compound having an alkyl group of 12 to 14 carbon atoms without additional ethylene oxide. Preferable examples of the component (A) include sodium mono- or dilauryl phosphate, diethanolamine mono- or dilauryl phosphate, triethanolamine mono- or dilauryl phosphate, sodium mono- or dimyristyl phosphate, potassium mono- or dimyristyl phosphate, diethanolamine mono- or dimyristyl phosphate, and triethanolamine mono- or dimyristyl phosphate.

As this component (A), compounds (I) and (II) are preferably used in a weight ratio of from 10:0 to 5:5, and particularly, from 10:0 to 7:3.

As the component (B) of the present invention, the amidoamine amphoteric surfactant (1) preferably has a lauroyl, a myristoyl, or a cocoyl group as $R_4CO-$ in the formula (III) or $R_5CO-$ in the formula (IV), and an alkali metal, particularly sodium, as M in these formulae. The hydroxysulfobetaine (2) of the formula (V) preferably has methyl groups as $R_5$ and $R_6$ and a lauryl or myristyl group as $R_4$, namely, it is preferable to use lauryldimethyl hydroxysulfobetaine or myristyldimethyl hydroxysulfobetaine.

As the compound (3), aliphatic lactylate or aliphatic glycolate shown by the formula (VI) is used. It is preferable that RCO in the formula (VI) has 12 to 18 carbon atoms, and examples of such compound include lauroyl lactylate, isolauroyl lactylate, myristoyl lactylate, isomyristoyl lactylate, oleoyl lactylate, isooleoyl lactylate, stearoyl lactylate, isostearoyl lactylate, lauroyl glycolate, isolauroyl glycolate, myristoyl glycolate, isomyristoyl glycolate, oleoyl glycolate, isooleoyl glycolate, stearoyl glycolate, isostearoyl glycolate and the like. Suitable salts include, for example, ammonium salts, alkali metal salts, and amine salts.

In the detergents of the present invention, when an amidoamine amphoteric surfactant (1) is used as the component (B), excellent effects can be obtained by using a betaine-type amphoteric surfactant together with the surfactant (1). This betaine-type amphoteric surfactant is preferably, for example, alkylbetaine, sulfobetaine, hydroxysulfobetaine, amidobetaine, amidosulfobetaine, or amidohydroxy sulfobetaine, which has an alkyl group of 8 to 20 carbon atoms. Of these hydroxysulfobetaine represented by the formula (V) of the compound (2) as the component (B) is particularly preferable.

The preferable mixing amount of the components (A), (B) and the betaine-type amphoteric surfactant in the detergent depends upon the kind of the compound selected as component (B). For example, when an amidoamine amphoteric surfactant (1) is used as the component (B) to form a liquid detergent, the component (A) is 5 to 50 weight % (hereinafter simply referred to as %), preferably 10 to 40%, of the composition and the component (B)-(1) is one or more parts but less than 20 parts by weight based on 20 parts of the component (A), preferably 5 to 15 parts. It is necessary to mix the betaine-type amphoteric surfactant of 0.1 or more parts but less than 10 parts by weight based on 20 parts of the component (A). When hydroxysulfobetaine (2) is used, the component (A) and the component (B)-(2) are mixed in the detergent composition in amounts such as to give proportions of 10 to 40% and 0.1 to 20%, respectively. When the compound (3) is used, the amount of component (A) used is 5 to 50% of the whole composition, preferably 10 to 40%, and the component (B)-(3) is 0.1 to 5%, preferably 0.1 to 3%. Use of the component (B)-(3) beyond this range fails to sufficiently achieve the intended effects.

In the dependent compositions of the present invention, it is possible as occasion demands to incorporate other components which are generally used in a detergent composition, for example, a humectant such as propylene glycol and glycerin, a viscosity modifier such as ethanol, an inorganic salt, a higher alcohol, hydroxymethyl cellulose, hydroxyethyl cellulose, hydroxypropyl cellulose, and methyl cellulose, a perfume, a colorant, an ultraviolet absorber, an antioxidant, an anti-dandruff agent, a germicide, a preservative, and water.

It is preferable to incorporate a phosphonic compound and dibutylhydroxy toluene in the above detergent in order to prevent coloring and deterioration of the perfume during storage at a higher temperature. This effect of these compounds of preventing coloring and perfume deterioration in detergent compositions containing a phosphate surfactant as a main component has been newly found by the present inventors.

Typical phosphonic compounds include compounds shown by the following formula (VII):

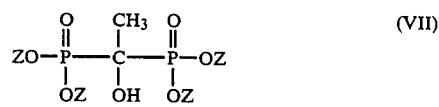

wherein Z represents a hydrogen atom or an alkali metal.

The amount of these phosphonic compounds added is preferably 0.2 to 5.0% relative to the total composition, preferably 0.3 to 2.0%. When the amount is less than 0.2%, they fail to prevent coloring and deterioration of the perfume even though they are used together with dibutylhydroxy toluene. if these compounds are added in excess of 5%, the odor of the phosphonic compounds themselves deteriorates and perfume deterioration cannot be prevented.

The amount of dibutylhydroxy toluene added is 0.001 to 0.5% relative to the total composition, preferably 0.01 to 0.1%. If this compound is added in an amount of under 0.001%, if fails to prevent coloring and perfume deterioration. If this compound is used in an amount exceeding 0.5%, the effect of preventing coloring and perfume deterioration substantially reaches an equilibrium state, even if it is used together with the above-described phosphonic compounds. Such amount is thus unfavorable.

There is no particular limitation with respect to the form in which the detergent compositions of the present invention are used. They can be provided in conventionally known forms, for example, liquid shampoo, cream face-washing agents, gel face-washing agents, and body shampoo.

The detergent compositions obtained by the present invention have excellent foaming characteristics such as foaming property, foaming power, and rapidity of foaming, as well as excellent low-temperature stability and detergency and mildness to the skin and hair. Therefore, these compositions can be effectively employed for shampoos, detergents for infants and the like which are required not only good detergency but also a low incidence of skin irritation.

The present invention is explained in detail with reference to the examples.

EXAMPLE 1

Liquid detergents having a formulation described below were prepared and their foaming properties were evaluated. The types and amount of the phosphate surfactants and amine amphoteric surfactants employed in the compositions are shown in Table 1.

(Formulation)

| | |
|---|---|
| Phosphate surfactant (Table 1) | 20% |
| Amidoamine amphoteric surfactant (Table 1) | Table 1 |
| Etahnol | 10% |
| Water | balance |

(Foaming property test)

1 g of the detergent composition was applied to a bunch of hair of 20 cm in length and 20 g in weight which has previously been moistened with water at 40° C. and they were evaluated in accordance with the following standards after foaming for 1 minute.
  O: Good foaming
  Δ: Medium foaming
  X: Poor foaming

TABLE 1

| Phosphate surfactant (A) | Ratio (A):(B) | Amidoamine amphoteric surfactant (B)1 | |
|---|---|---|---|
| | | Formula (III) $R_4 = C_{11}H_{23}$ $M = Na$ | Formula (IV) $R_5 = C_{11}H_{23}$ $M = Na$ |
| Potassium monolauryl phosphate | 20:0 | X | X |
| | 20:5 | O | O |
| | 20:10 | O | O |
| | 20:15 | O | O |
| | 20:20 | Δ | Δ |
| | 20:25 | X | X |
| Triethanolamine monolauryl phosphate | 20:0 | X | X |
| | 20:5 | O | O |
| | 20:10 | O | O |
| | 20:15 | O | O |
| | 20:20 | Δ | Δ |
| | 20:25 | X | X |
| Triethanolamine polyoxyethylene (3) monomyristyl phosphate | 20:0 | X | X |
| | 20:5 | O | O |
| | 20:10 | O | O |
| | 20:15 | O | O |
| | 20:20 | Δ | Δ |
| | 20:25 | X | X |

EXAMPLE 2

Liquid detergents having a formulation shown in Table 2 were prepared and their foaming power, the appearance of their foams, and their susceptibility to skin irritation were tested by the following methods. The results are shown in Table 2.

(Foaming power)

0.5% of lanolin as an artificial dirt was added to a 3% aqueous solution of the detergent composition, and agitated by a flat propeller in a cylinder at 40° C. and at a rotational speed of 1000 rpm for 5 minutes. The rotation of the propeller was reversed at every 10 seconds. The foaming power is indicated by the amount of foam (ml) remained 30 seconds after completion of the agitation.

(Appearance of foam)

The appearance of the foam was evaluated in accordance with the following standards with respect to "creaminess".
  O: Creamy foam
  Δ: Slightly creamy foam
  X: Rough foam (Irritation to skin)

10 subjects were asked to wash their faces with 3 g of the detergent compositions and questioned about the presence of abnormalities such as feelings of tautness and tingling of the skin during washing and after washing and drying. The degree of skin irritation was evaluated from the number of subjects complaining of abnormalities in accordance with the following criteria:
  O: Less than 3 subjects out of 10 complaining of abnormalities.
  Δ: 4 to 7 subjects out of 10 complaining of abnormalities.
  X: More than 8 subjects out of 10 complaining of abnormalities.

TABLE 2

| (Comparative Products) Detergent component** | (content) | Foaming power (ml) | Appearance of foam | Skin irritation |
|---|---|---|---|---|
| Triethanolamine monolauryl phosphate | (25%) | 9.1 | X | O |
| Triethanolamine monolauryl phosphate Diethanolamine laurate | (20%) (5%) | 32.7 | X | O |
| Triethanolamine monolauryl phosphate Lauryl betaine | (20%) (5%) | 41.8 | X | O |
| Triethanolamine monolauryl phosphate Tertiary amidoamine* | (20%) (5%) | 116.4 | Δ | O |

TABLE 2-continued

| (Comparative Products) | | | | |
|---|---|---|---|---|
| Detergent component** | (content) | Foaming power (ml) | Appearance of foam | Skin irritation |
| Triethanolamine lauryl sulfate | (25%) | 148.2 | O | X |
| Triethanolamine monolauryl phosphate<br>Amidoamine amphoteric surfactant<br>[Formula (III), $R_4 = C_{11}H_{23}$, M = Na] | (20%)<br>(5%) | 190.0 | O | O |
| Triethanolamine monolauryl phosphate<br>Amidoamine amphoteric surfactant<br>[Formula (IV), $R_5 = C_{11}H_{23}$, M = Na] | (20%)<br>(5%) | 207.3 | O | O |

$$*C_{11}H_{23}CON \begin{matrix} CH_2CH_2NHCH_2COONa \\ \\ CH_2CH_2OH \end{matrix}$$

**The residue was water.

As seen from Table 2, it is evident that the detergents of the present invention exhibit excellent foaming characteristics and low skin irritation.

EXAMPLE 3

Shampoo compositions A, B and C having the following formulations were prepared and shampooing tests were carried out on 20 long-haired women, their organoleptic evaluations being compared with each other. The results are shown in Table 3.

Shampoo A (Inventive product)

| | |
|---|---|
| Triethanolamine monolauryl phosphate | 18.0% |
| Amidoamine amphoteric surfactant | 5.0% |
| (In formula (III), $R_4 = C_{11}H_{23}$, M = Na) | |
| Preservative (methylparaben) | 0.1% |
| Perfume | 0.3% |
| Colorant | small amount |
| Water | balance |
| | (pH 7.5) |

Shampoo B (Comparative products)

| | |
|---|---|
| Triethanolamine monolauryl phosphate | 18.0% |
| Diethanolamine laurate | 5.0% |
| Preservative (methylparaben) | 0.1% |
| Perfume | 0.3% |
| Colorant | small amount |
| Water | balance |
| | (pH 7.5) |

Shampoo C (Comparative product)

| | |
|---|---|
| Triethanolamine monolauryl phosphate | 18.0% |
| Preservative (methylparaben) | 0.1% |
| Perfume | 0.3% |
| Colorant | small amount |
| Water | balance |
| | (pH 7.5) |

TABLE 3

| | Type of shampoo considered best | | | |
|---|---|---|---|---|
| Evaluation item | A | B | C | No preference |
| Easiness of foaming | 19 | 1 | 0 | 0 |
| Creaminess of foam | 19 | 0 | 0 | 1 |
| Smoothness with which fingers pass through hair during washing | 18 | 1 | 0 | 1 |
| Easiness of rinsing | 17 | 1 | 0 | 2 |
| Easiness of hair banding | 18 | 0 | 0 | 2 |

EXAMPLE 4

Solid detergent (for infants)

(Formulation)

| | |
|---|---|
| Sodium monolauryl phosphate | 25% |
| Sodium dilaury phosphate | 5% |
| Sodium monomyristyl phosphate | 32% |
| Sodium dimyristyl phosphate | 5% |
| Amidoamine amphoteric surfactant<br>[In formula (III), $R_4 = C_{11}H_{23}$, M = Na] | 20% |
| Perfume | 0.3% |
| Water | balance |

A solid detergent exhibiting mildness to skin, rapidity of foaming, and excellent foaming power was obtained from the above-described formulation.

EXAMPLE 5

Shampoo compositions having the formulation shown in Table 4 were prepared and their foaming power and the feeling of the foams produced were evaluated. The foaming power was measured at 1% concentration of each detergent composition. The results are shown in Table 4.

TABLE 4

| | Composition (%) | | | | | | |
|---|---|---|---|---|---|---|---|
| | Inventive product | | | | | | Comparative product |
| | 1 | 2 | 3 | 4 | 5 | 6 | |
| Triethanolamine monolauryl phosphate | 20 | 20 | 20 | 20 | 20 | 20 | 20 |
| Amidoamine amphoteric surfactant [In formula(IV), $R_5 = C_{11}H_{23}$, | 8 | 6 | 5 | 4 | 2 | 10 | — |

TABLE 4-continued

| | Composition (%) | | | | | | |
|---|---|---|---|---|---|---|---|
| | Inventive product | | | | | | Comparative product |
| | 1 | 2 | 3 | 4 | 5 | 6 | |
| M = Na] Lauryldimethyl hydroxy-sulfobetaine | 8 | 4 | 5 | 6 | 8 | — | 10 |
| Perfume, pH regulator, Water | | | | balance | | | |
| Foaming power (ml) | 185.9 | 193.8 | 200.0 | 193.8 | 173.4 | 153.1 | 125.0 |
| Feeling of foam | O | O | O | O | O | O | Δ |

EXAMPLE 6

Detergent compositions having the formulations shown in Table 5 were prepared and their foaming power, the feeling of the foam, rapidity of foaming, and their low-temperature stability were tested. The results are shown in Table 5.

(1) Foaming test 0.5% of lanolin as an artificial dirt was added to 3% aqueous solution (water of 4°DH) of the detergent composition, and agitated by a flat propeller in a cylinder at 40° C. and at a rotational speed of 1000 rpm for 5 minutes. The rotation of the propeller was reversed at every 10 seconds; their foaming power was evaluated from the amount of foam remained 30 seconds after completion of the agitation.

(2) Shampoo test

1. Foaming property

A tress of human hair, 20 cm long and 20 g in weight, was soaked in hot water at 40° C. and the detergent composition was then throughly applied to the hair. The foaming property of each composition after foaming for 1 minute was evaluated in accordance with the following criteria:
 O: Good foaming
 Δ: Medium foaming
 X: Poor foaming 2. Feeling The hairs which had been foamed in the above test 1 regarding foaming property were rinsed with water and the feeling of each was evaluated in accordance with the following criteria:

O: Good
Δ: Medium
X: Poor

3. Test of low-temperature stability

The liquid detergent was poured into a glass bottle, and was preserved at −5° C. for 10 days. Then the appearance of the agent was evaluated in accordance with the following criteria:
 O: Transparent
 Δ: Slightly cloudy
 X: Precipitates produced

TABLE 5

| Detergent composition* | Inventive product (1) | Comparative product | | | |
|---|---|---|---|---|---|
| | | (1) | (2) | (3) | (4) |
| Triethanolamine monolauryl phosphate | 20 | 20 | 20 | 20 | 20 |
| Lauryldimethyl hydroxy-sulfobetaine | 5 | | | | |
| Diethanolamine laurate | | 5 | | | |
| Laurylcarboxybetanine | | | 5 | | |
| Laurylsulfobetaine | | | | 5 | |
| Foaming power (ml) | 182 | 10 | 36 | 40 | 132 |
| Feeling (shampoo test) | O | X | Δ | Δ | Δ |
| Foaming property (shampoo test) | O | X | X | X | Δ |
| Low-temperature stability | O | X | X | X | Δ |

*The residue was water. The pH was regulated at 7 by an acid or an alkali as required.

EXAMPLE 7

Detergent compositions having the formulations shown in Table 6 were prepared and their properties were tested. The results are shown in Table 6.

TABLE 6

(weight %)

| Detergent composition* | Inventive product | | | | | | Comparative product | | | |
|---|---|---|---|---|---|---|---|---|---|---|
| | (2) | (3) | (4) | (5) | (6) | (7) | (5) | (6) | (7) | (8) |
| Sodium polyoxyethylene(1) mono-lauryl phosphate | 20 | 20 | 15 | | 20 | | 20 | 20 | 20 | 20 |
| Potassium mono/di(80/20)-lauryl phosphate | | | | 20 | | 20 | | | | |
| Lauryldimethyl hydroxysulfobetaine | 3 | 5 | 10 | | | | | | | |
| Myristyldimethyl hydroxysulfobetaine | | | | 4 | | | | | | |
| Coconut oil alcohol dimethyl hydroxysulfobetaine | | | | | 7 | | | | | |
| Lauryldiethyl hydroxysulfobetaine | | | | | | 5 | | | | |
| Diethanolamido laurate | | | | | | | 5 | | | 10 |
| Laurylcarboxybetaine | | | | | | | | 5 | | |
| Laurylsulfobetaine | | | | | | | | | 5 | |
| Foaming power (ml) | 164 | 182 | 190 | 178 | 176 | 180 | 36 | 40 | 132 | 55 |
| Feeling (shampoo test) | O | O | O | O | O | O | X | X | Δ | X |
| Foaming property (shampoo test) | O | O | O | O | O | O | X | X | Δ | X |

TABLE 6-continued

| Detergent composition* | Inventive product | | | | | | Comparative product (weight %) | | | |
|---|---|---|---|---|---|---|---|---|---|---|
| | (2) | (3) | (4) | (5) | (6) | (7) | (5) | (6) | (7) | (8) |
| Low-temperature stability | O | O | O | O | O | O | X | X | Δ | X |

*The residue was water. The pH was regulated at 7 by an acid or an alkali as required.

EXAMPLE 8

Liquid shampoo having the formulations shown in Table 7 were prepared and their properties were evaluated by the methods described below. The results are shown in Table 7.

(1) Method of evaluating the feeling of foams 30 g of human hair was moistened with water having a temperature of 40° C. and 20 g of the water was impregnated. Then, the hair was washed by using 1 g of the shampoo composition and the feeling of the foam produced was organoleptically evaluated by a panel consisting of 20 women subjects. The smoothness with which the fingers passed through the hair during hair-washing was evaluated as "foam smoothness" and the appearance of the liquid was evaluated from the viewpoint of "creaminess".

(2) Method of evaluated feeling and gloss of finished hair 30 g of human hair was moistened with water having a temperature of 40° C. and 20 g of the water was impregnated. The hair was then washed by using 1 g of the shampoo composition, rinsed with flowing water squeezed, dried with a drier, and organoleptically evaluated by a panel consisting of 20 women subjects with respect to the feeling (smoothness) and the gloss.

(3) Method of measuring detergency

Dirty clothes artificially soiled with oil were soaked in 3% aqueous shampoo solution, agitated for 10 minutes at 40° C. by a tugot meter, and rinsed with flowing water. The reflectance displayed by each of these dirty clothes was measured at 460 nm by a colorimeter before and after washing with a view of calculating the effective derging rates.

TABLE 7

| Component (%) | Comparative Product 1 | Inventive product | | | | | | | | Comparative product | | | | | | |
|---|---|---|---|---|---|---|---|---|---|---|---|---|---|---|---|---|
| | | 2 | 3 | 4 | 5 | 6 | 7 | 8 | 9 | 10 | 11 | 12 | 13 | 14 | 15 | 16 |
| Triethanolamine mono/di(7/3)-lauryl phosphate | 17 | 17 | 17 | 17 | 17 | 17 | 17 | 17 | 17 | | | | | | | |
| Triethanolamine lauryl sulfate | | | | | | | | | | 17 | 17 | 17 | 17 | 17 | 17 | 17 |
| Sodium polyoxyethylene($\overline{EO} \approx 3$) lauryl sulfate | | | | | | | | | | | | | | | | |
| Stearoyl lactylate | | 0.5 | 2 | | | | | | | 0.5 | 2 | | | | | |
| Isostearoyl lactylate | | | | 0.5 | 2 | | | | | | | 0.5 | 2 | | | |
| Lauroyl lactylate | | | | | | 0.5 | 2 | | | | | | | 0.5 | 2 | |
| Myristoyl glycolate | | | | | | | | 0.5 | 2 | | | | | | | |
| Water | 83 | 82.5 | 81 | 82.5 | 81 | 82.5 | 81 | 82.5 | 81 | 83 | 82.5 | 81 | 82.5 | 81 | 82.5 | 81 |
| Feeling of foam Smoothness | X | Δ | O | Δ | O | Δ | O | Δ | O | X | X | Δ | X | Δ | X | Δ |
| Creaminess | X | Δ | O | Δ | O | Δ | O | Δ | O | X | X | Δ | X | Δ | X | Δ |
| Finish Smoothness | X | Δ | O | Δ | O | Δ | O | Δ | O | X | X | Δ | X | Δ | X | Δ |
| Gloss | X | Δ | O | Δ | O | Δ | O | Δ | O | X | X | Δ | X | Δ | X | Δ |
| Derging rate (%) | 53 | 56 | 63 | 58 | 64 | 54 | 58 | 55 | 60 | 56 | 58 | 59 | 55 | 58 | 54 | 56 |

| Component (%) | Comparative product | | | | | | | | | | |
|---|---|---|---|---|---|---|---|---|---|---|---|
| | 17 | 18 | 19 | 20 | 21 | 22 | 23 | 24 | 25 | 26 | 27 |
| Triethanolamine mono/di(7/3)-lauryl phosphate | | | | | | | | | | | |
| Triethanolamine lauryl sulfate | 17 | 17 | | | | | | | | | |
| Sodium polyoxyethylene ($\overline{EO} \approx 3$) lauryl sulfate | | | 17 | 17 | 17 | 17 | 17 | 17 | 17 | 17 | 17 |
| Stearoyl lactylate | | | | 0.5 | 2 | | | | | | |
| Isostearoyl lactylate | | | | | | 0.5 | 2 | | | | |
| Lauroyl lactylate | | | | | | | | 0.5 | 2 | | |
| Myristoyl glycolate | | | | | | | | | | 0.5 | 2 |
| Water | 82.5 | 81 | 83 | 82.5 | 81 | 82.5 | 81 | 82.5 | 81 | 82.5 | 81 |
| Feeling of foam Smoothness | X | Δ | X | X | Δ | X | Δ | X | Δ | X | Δ |
| Creaminess | X | Δ | X | X | Δ | X | Δ | X | Δ | X | Δ |
| Finish Smoothness | X | Δ | X | X | Δ | X | Δ | X | Δ | X | Δ |
| Gloss | X | Δ | X | X | Δ | X | Δ | X | Δ | X | Δ |
| Derging rate (%) | 58 | 57 | 57 | 59 | 60 | 58 | 62 | 57 | 60 | 56 | 59 |

Note:
Evaluation criteria: O good, Δ medium, X poor
In these tables, the lactylate and glycolate used were sodium salts of $\bar{p} = 2$.

As seen from Table 7, combination use of phosphate surfactants with aliphatic lactylates or aliphatic glycolates produces a shampoo composition which generates foam of excellent creaminess, is capable of giving hair glossy after drying, and has excellent detergency.

EXAMPLE 9

A liquid shampoo having the formulation shown in Table 8 was prepared and the effect for removal of dandruff was tested by the method described below. The results are shown in Table 9.

TABLE 8

| Component | Comparative product | Inventive product (%) |
|---|---|---|
| Sodium nomo/di(8/2)lauryl phosphate | 20 | 20 |
| Isostearoyl lactylate (sodium salt, $\bar{p} = 2$) | — | 1 |
| Perfume | 0.3 | 0.3 |
| Water | 79.7 | 78.7 |

Method of measuring dandruff-removing effectiveness

Measurements were carried out for 10 women panelists. 2 ml of a 10% shampoo solution was poured into a cups attached on the scalp of each panelist. After 30 seconds, several drops of a fuchsin/crystal violet mixture solution were added to the shampoo to calculate the numbers of horny cells by use of a hemocytometer. The removal rate of dandruff is expressed by the counted horny cells. Horny cells were counted at 3 portions for each of the inventive shampoo and the comparative shampoo for each of the panelists.

TABLE 9

| Shampoo composition | Panelist Horny cell number ($\times 10^6$) | | | | | | | | | |
|---|---|---|---|---|---|---|---|---|---|---|
| | 1 | 2 | 3 | 4 | 5 | 6 | 7 | 8 | 9 | 10 |
| Comparative product | 3.3 | 1.7 | 1.1 | 3.0 | 2.9 | 2.7 | 1.9 | 2.2 | 3.1 | 1.4 |
| Inventive product | 4.6 | 2.7 | 1.6 | 5.1 | 3.1 | 3.5 | 2.4 | 3.7 | 4.9 | 1.7 |

As seen from Table 9, combination use of a phosphate surfactant with a lactylate can produce a shampoo having an excellent ability to remove dandruff.

EXAMPLE 10

Paste Shampoo (Formulation)

| | |
|---|---|
| Sodium mono/di(7/3)lauryl phosphate | 20% |
| Lauroyl lactylate (sodium salt, $\bar{p} = 2$) | 2% |
| Carbopole 941 (carboxyvinyl polymer) | 0.5% |
| NaCl | 1% |
| Perfume | 0.3% |
| Water | balance |

The above composition provided a shampoo which produces foam with an extremely excellent creaminess, is capable of giving hair glossy after drying, and which has an excellent ability to remove dandruff.

EXAMPLE 11

Liquid Shampoo (Formulation)

| | |
|---|---|
| Sodium polyoxyethylene ($\overline{EO} = 2$) mono/di(7/3)lauryl phosphate | 18% |
| Lauroyl lactylate (sodium salt, $\bar{p} = 2$) | 3% |
| Diethanolamine laurate | 5% |
| Perfume | 0.3% |
| Water | balance |

The above composition provided a shampoo composition which produces foam with an extremely excellent creaminess, is capable of giving hair glossy after drying, and which has an excellent ability to remove dandruff.

EXAMPLE 12

Detergent compositions having the formulations shown in Table 10 were prepared and tested with respect to their ability of preventing coloring and perfume deterioration. The results are shown in Table 10.

(1) Effect of coloring prevention

The detergent composition prepared was stored at 50° C. for 20 days and its color was compared with that of freshly prepared composition. The coloring prevention effect was evaluated visually in accordance with the following criteria:

O: Good without any change in color tone
Δ: Unusable with some change in color tone
X: Unusable with a remarkable change in color tone (2) Effect of perfume deterioration The detergent composition prepared was stored at 50° C. for 20 days and the perfume deterioration which occurred was organoleptically evaluated with respect to odor by panelists; the freshly prepared cleaning agents was used as a standard.

O: Good without any change in perfume strength
Δ: Usable with some change in perfume strength
X: Unusable with a remarkable change in perfume strength

TABLE 10

| Detergent composition | 1* | 2* | 3 | 4 | 5 | 6 | 7 | 8 | 9 | 10 (weight %) |
|---|---|---|---|---|---|---|---|---|---|---|
| Triethanolamine monolauryl phosphate[1] | 15.0 | 15.0 | 15.0 | | | | 15.0 | 15.0 | 15.0 | 15.0 |
| Triethanolamine mono/di-lauryl phosphate[2] | | | | 15.0 | | | | | | |
| Triethanolamine monomyristyl phosphate | | | | | 15.0 | | | | | |
| Sodium monolauryl phosphate | | | | | | 15.0 | | | | |
| Lauryldimethyl hydroxysulfo-betaine | 5.0 | | | | | | | | | |
| Amidoamine amphoteric surfactant [In formula(IV), $R_5 = C_{11}H_{23}$, M = Na] | | 5.0 | | | | | | | | |
| 1-Hydroxyethylidene-1,1-di-phosphonate | 1.0 | 1.0 | 1.0 | 1.0 | 1.0 | 1.0 | 1.0 | | | |
| Dibutylhydroxy toluene | 0.05 | 0.05 | 0.05 | 0.05 | 0.05 | 0.05 | | 0.5 | | |
| Disodium ethylenediaminetetra-acetate | | | | | | | | | 1.0 | |
| α-Tocopherol | | | | | | | | | | 1.0 |
| Perfume | 0.3 | 0.3 | 0.3 | 0.3 | 0.3 | 0.3 | 0.3 | 0.3 | 0.3 | 0.3 |
| Water | | | | | balance | | | | | |
| Freedom from coloring | O | O | O | O | O | O | Δ | Δ | X | X |
| Freedom from perfume | O | O | O | O | O | O | X | X | X | X |

TABLE 10-continued

| Detergent composition | 1* | 2* | 3 | 4 | 5 | 6 | 7 | 8 | (weight %) 9 | 10 |
|---|---|---|---|---|---|---|---|---|---|---|
| deterioration | | | | | | | | | | |

Note: (Table 10)
*denotes the inventive composition.
(1) triethanolamine monolauryl phosphate:triethanolamine dilauryl phosphate = 100:0
(2) triethanolamine monolauryl phosphate:triethanolamine dilauryl phosphate = 70:30

EXAMPLE 13

As shown in Table 11, detergent compositions comprising 1-hydroxyethylidene-1,1-diphosphate and dibutylhydroxy toluene in different proportion were prepared and tested with respect to their freedom from coloring and perfume deterioration. The results are shown in Table 11.

TABLE 11

| Detergent composition | 11* | 12* | 13 | 14 | 15 | 16 | 17 |
|---|---|---|---|---|---|---|---|
| Sodium polyoxyethylene(EO ≈ 1) mono/dilaurylphosphate (3) | 15.0 | 15.0 | 15.0 | 15.0 | 15.0 | 15.0 | 15.0 |
| Lauryldimethyl hydroxysulfobetaine | 5.0 | | | | | | |
| amidoamine amphoteric surfactant [In formula(IV), $R_5 = C_{11}H_{23}$, M = Na] | | 5.0 | | | | | |
| 1-hydroxyethylidene-1,1-diphosphate | 0.5 | 0.5 | 0.5 | 2.0 | 1.0 | 6.0 | 0.1 |
| Dibutylhydroxy toluene | 0.01 | 0.01 | 0.01 | 0.1 | 0.0005 | 0.05 | 0.1 |
| Perfume | 0.3 | 0.3 | 0.3 | 0.3 | 0.3 | 0.3 | |
| Water | | | | balance | | | |
| Prevention of coloring | O | O | O | O | X | O | X |
| Prevention of perfume deterioration | O | O | O | O | X | X | X |

Note
*denotes the inventive product.
(3) sodium polyoxyethylene monolauryl phosphate:sodium polyoxyethylene dilauryl phosphate = 70:30

What is claimed is:

1. A detergent composition, the major active detergent component of which consists of:
   (A) 10–40 weight % of at least one phosphate surfactant selected from the group consisting of compounds of formulas (I) and (II):

$$R_1(OCH_2CH_2)_l\text{—}O\text{—}\underset{OX}{\overset{\overset{O}{\|}}{P}}\text{—}OY \quad (I)$$

$$\begin{array}{c} R_2\text{—}(OCH_2CH_2)_m\text{—}O \\ \\ R_3\text{—}(OCH_2CH_2)_n\text{—}O \end{array} \!\!\!\!\begin{array}{c} O \\ \| \\ P\text{—}OX \end{array} \quad (II)$$

wherein $R_1$, $R_2$ and $R_3$ each independently represent a saturated or unsaturated hydrocarbon group having 8 to 18 carbon atoms; X and Y each independently represent a hydrogen atom, an alkali metal, ammonium, or an alkanol amine having at least one hydroxyalkyl group having 2 to 3 carbon atoms; and l, m and n each independently represent an integer of 0 to 10, and (B) a compound selected from the group consisting of the following compounds (1) to (3):
   (1) an amidoamine amphoteric surfactant of formula (III) or (IV):

$$R_4\text{—}CONHCH_2CH_2\underset{CH_2CH_2COOM}{NCH_2CH_2OH} \quad (III)$$

$$R_5\text{—}CONHCH_2CH_2\underset{CH_2COOM}{NCH_2CH_2OH} \quad (IV)$$

in which $R_4$ and $R_5$ each independently represent a saturated or unsaturated hydrocarbon group having 7 to 19 carbon atoms; M represents a hydrogen atom, an alkali metal, ammonium, or an alkanol amine having at least one hydroxyalkyl group having 2 to 3 carbon atoms, wherein said amidoamine amphoteric surfactant (B)-(1) is present in at least one part to less than 20 parts by weight based on 20 parts of said component (A), (2) 0.1–20 weight % of a hydroxysulfobetaine of formula (V):

$$R_6\text{—}\underset{R_8}{\overset{R_7}{N^+}}\text{—}CH_2\underset{OH}{CH}\text{—}CH_2\text{—}SO_3^- \quad (V)$$

wherein $R_6$ represents a saturated or unsaturated hydrocarbon group having 8 to 18 carbon atoms, and $R_7$ and $R_8$ each independently represent a methyl or ethyl group, and (3) 0.1–5 weight % of a compound of formula (VI) and its salt:

$$RCO(O.CHCO)_p\overset{A}{|}OH \quad (VI)$$

wherein RCO represents a linear or branched aliphatic acyl group having 6 to 22 carbon atoms; A represents $CH_3$ or a hydrogen atom, and p represents an integer of 1 to 3.

2. A detergent composition, the major active detergent of which consists of:
(A) 10–40 weight % of at least one phosphate surfactant selected from the group consisting of compounds of formulas (I) and (II):

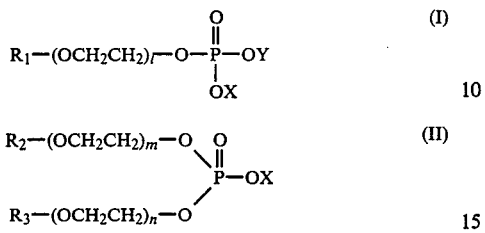

wherein $R_1$, $R_2$ and $R_3$ each independently represent a saturated or unsaturated hydrocarbon group having 8 to 18 carbon atoms; X and Y each independently represent a hydrogen atom, an alkali metal, ammonium, or an alkanol amine having at least one hydroxyalkyl group having 2 to 3 carbon atoms; and l, m and n each independently represent an integer of 0 to 10, and (B) from 0.1–20 weight % of a hydroxysulfobetaine of the formula:

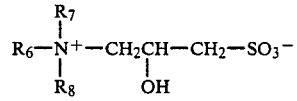

wherein $R_6$ represents a saturated or unsaturated hydrocarbon group having 8 to 18 carbon atoms, and $R_7$ and $R_8$ each independently represent a methyl or ethyl group.

* * * * *